United States Patent
Erdler et al.

(10) Patent No.: US 9,093,690 B2
(45) Date of Patent: Jul. 28, 2015

(54) SENSOR FUEL CELL

(75) Inventors: Gilbert Erdler, Freiberg (DE); Holger Reinecke, Emmendingern (DE); Claas Mueller, Freiburg (DE); Mirko Frank, Pfaffenmeiler (DE)

(73) Assignee: Micronas GmbH, Freiburg (DE)

( * ) Notice: Subject to any disclaimer, the term of this patent is extended or adjusted under 35 U.S.C. 154(b) by 1990 days.

(21) Appl. No.: 12/266,214

(22) Filed: Nov. 6, 2008

(65) Prior Publication Data

US 2009/0136815 A1    May 28, 2009

(30) Foreign Application Priority Data

Nov. 6, 2007  (EP) .................................... 07021539

(51) Int. Cl.
  *H01M 8/10*   (2006.01)
  *G01N 27/407*  (2006.01)
  *H01M 8/04*   (2006.01)
(52) U.S. Cl.
  CPC ......... *H01M 8/1097* (2013.01); *G01N 27/4073* (2013.01); *H01M 8/04089* (2013.01); *H01M 8/04216* (2013.01); *H01M 2300/0071* (2013.01); *Y02E 60/521* (2013.01)
(58) Field of Classification Search
  USPC .................................................. 204/410, 424
  See application file for complete search history.

(56) References Cited

U.S. PATENT DOCUMENTS

| 3,338,746 A | 4/1967 | Plust et al. |
| 3,400,305 A | 9/1968 | Coffman |
| 4,164,172 A | 8/1979 | Anderten et al. |
| 4,661,211 A * | 4/1987 | Petty-Weeks ................. 205/783 |
| 4,863,813 A | 9/1989 | Dyer |
| 4,908,118 A | 3/1990 | Ammende et al. |
| 5,302,274 A * | 4/1994 | Tomantschger et al. ...... 204/412 |
| 6,028,414 A | 2/2000 | Chouinard et al. |

(Continued)

FOREIGN PATENT DOCUMENTS

| DE | 19908532 | 4/2000 | |
| DE | 102 55 736 | 6/2004 | ........................... 8/2 |

(Continued)

OTHER PUBLICATIONS

Nogami et al. "Hydrogen Sensor Prepare Using Fast Proton-Conducting Glass Films", Sensors and Actuators, vol. 120, No. 1, Dec. 14, 2006, pp. 266-269.

(Continued)

*Primary Examiner* — Kaj K Olsen
(74) *Attorney, Agent, or Firm* — Muncy, Geissler, Olds & Lowe, P.C.

(57) ABSTRACT

The invention relates to a sensor fuel cell that can be activated by a first substance ($O_2$) in its environment. The sensor fuel cell includes a catalytically active anode, a cathode that has a cathode surface at least partially exposed to the environment, and a proton-conductive membrane located between the anode and the cathode so as to convey protons through from the anode to the cathode. An anode surface of the anode is at least partially exposed to the environment for access of at least one second substance ($H_2$) from the environment to the anode. Such a disposition enables access of a first reactant in the form for example of oxygen from the ambient air to the cathode, and additionally access of a second reactant in the form for example of hydrogen from the ambient air to the free surface of the anode.

12 Claims, 1 Drawing Sheet

(56) References Cited

U.S. PATENT DOCUMENTS

| | | | |
|---|---|---|---|
| 6,057,051 A | 5/2000 | Uchida et al. | |
| 6,096,453 A * | 8/2000 | Grunwald | 429/212 |
| 6,146,782 A * | 11/2000 | Wendt et al. | 429/506 |
| 6,160,278 A | 12/2000 | Liu et al. | |
| 6,306,285 B1 * | 10/2001 | Narayanan et al. | 205/787 |
| 6,312,846 B1 | 11/2001 | Marsh | |
| 6,326,097 B1 | 12/2001 | Hockaday | |
| 6,337,009 B1 * | 1/2002 | Nadanami et al. | 205/775 |
| 6,488,836 B1 * | 12/2002 | Nakata et al. | 205/784 |
| 6,506,511 B1 | 1/2003 | Lakeman et al. | |
| 6,641,862 B1 * | 11/2003 | Grot | 427/115 |
| 2001/0016283 A1 | 8/2001 | Shiraishi et al. | |
| 2001/0033959 A1 | 10/2001 | Ovshinsky et al. | |
| 2002/0098399 A1 | 7/2002 | Keppeler | |
| 2002/0168560 A1 | 11/2002 | Mukerjee et al. | |
| 2003/0003347 A1 | 1/2003 | D'Arrigo et al. | |
| 2003/0024813 A1 * | 2/2003 | Taniguchi | 204/424 |
| 2003/0157389 A1 | 8/2003 | Kornmayer | |
| 2003/0170520 A1 | 9/2003 | Fujii et al. | |
| 2004/0209132 A1 * | 10/2004 | Nelson et al. | 429/19 |
| 2006/0127716 A1 | 6/2006 | Lehmann | |

FOREIGN PATENT DOCUMENTS

| | | | |
|---|---|---|---|
| EP | 1037183 | 9/2000 | |
| WO | WO 01/69228 | 9/2001 | 27/414 |
| WO | WO 02/30810 | 4/2002 | 3/6 |
| WO | WO 2005/008824 | 1/2005 | 8/18 |

OTHER PUBLICATIONS

Wilbertz et al. "Suspended-Gate-and Lundstrom-FET Integrated on a CMOS-Chip", Sensors and Actuators, vol. 123-124, Sep. 23, 2005, pp. 2-6.

CMOS (complementary metal-oxide semiconductor), 2000, In Collins Dictionary of Computing. http://www.credoreference.com/entry/1252056.

* cited by examiner

SENSOR FUEL CELL

PRIORITY INFORMATION

This patent application claims priority from European patent application 07 021 539.7 filed Nov. 6, 2007, which is hereby incorporated by reference.

BACKGROUND OF THE INVENTION

The invention relates to a sensor fuel cell, and in particular to a sensor fuel cell located on a semiconductor.

German patent application DE 102 55 736 A1 describes, among other things, a sensor fuel cell that can be activated by a first substance situated in its environment. The sensor fuel cell exhibits, on a substrate, a catalytically active anode, a cathode that exhibits a cathode surface freely exposed to the environment, and a proton-conductive membrane that is situated between the anode and the cathode so as to convey protons through from the anode to the cathode. In this disposition the anode is fabricated from palladium and saturated with hydrogen. If atmospheric oxygen from the environment reaches the cathode, a voltage or a current flow is produced when appropriate circuit elements are present.

A fundamental idea is that one of the two electrodes (i.e., the anode or the cathode) is disposed directly on the substrate and completely covered by the membrane and the other electrode. The covered electrode is a reservoir for one of the substances that is employed as reactant in the fuel cell. If oxygen is stored as reactant in or on the covered electrode, the fuel cell can be employed as a sensor and warning device in case of the occurrence of hydrogen in the environment.

A fundamental idea, however, is to fashion a chip-integrable fuel cell on a silicon substrate in the form of a palladium film as an integrated (n) hydrogen reservoir, in order to furnish a power supply source. It is essential that the covered electrode on the substrate is charged with an adequate quantity of the substance or reactant before the membrane and the second electrode are fashioned thereover in completely overlapping fashion. It is accordingly disadvantageous that such a disposition or sensor fuel cell has only a limited lifetime or only a limited service life. Such a sensor fuel cell is no longer employable and must be replaced once the reactant on the covered electrode has been consumed.

The paper entitled "*Suspended-Gate- and Lundström-FET Integrated on a CMOS-Chip*," by Ch. Wilbertz, H. P. Frerichs, I. Freund and M. Lehmann, Sensors & Actuators A 123-124 (2005), 2-6, describes a suspended gate and a Lundström FET on CMOS substrates. In the case of the Lundström FET a hydrogen-sensitive film is situated on the gate electrode; in the suspended gate FET, the hydrogen-sensitive film is situated a well-defined distance above the gate electrode. Hydrogen detection takes place via a change in the work function of the hydrogen-sensitive electrodes, by which a threshold voltage of the transistors is altered. The resolution limits of Lundström sensors are typically in the low ppm range while the resolution limit of the suspended gate FET is in the low percent range.

In such Lundström and SG FET sensors it is disadvantageous that these continuously deliver an output signal, which can underlie a baseline drift. The resolution limit of sensors fabricated on this basis is in the ppm and low percent range. Lundström and SG FET sensors are active systems, so that they must be continuously supplied with energy or partly heated in order to operate them.

There is a need for a sensor fuel cell that enables a broader range of applications and at the same time is relatively simple in structure.

SUMMARY OF THE INVENTION

According to an aspect of the invention, a sensor fuel cell can be activated by a first ambient substance and includes a catalytically active anode and a cathode. The cathode includes a cathode surface at least partially exposed to the environment, and a proton-conductive membrane that is disposed between the anode and the cathode to convey protons through from the anode to the cathode. An anode surface of the anode is at least partially exposed to the environment for access of at least one second ambient substance to the anode.

Such a disposition enables access to the cathode of a first reactant in the form for example of oxygen from the ambient air, and also access to the free surface of the anode of a second reactant in the form for example of a hydrocarbon-containing substance or in particular hydrogen from the ambient air. Advantageously, in a remarkably simple way, self-sustaining and long service is enabled because there is no need to integrate in the sensor any hydrocarbon source or oxygen source that becomes exhausted.

Thus both reactants are supplied from outside from the environment to the electrodes. The fuel cell reaction comes about because of the catalytically active electrodes, where the current generated or the voltage generated is directly related to the ambient concentration of the reactants.

The membrane and the cathode are sized and disposed on the anode surface so that the anode surface is at least partially not covered by the membrane and the cathode. Between an outer circumference of the membrane and an outer circumference of the cathode there preferably remains, in an extent in a plane of the anode surface, a free clearance to an outer circumference of the anode surface, via which the anode surface is accessible to the environment for access of at least one second ambient substance. Such developments already leave ample scope for enabling access of the second substance to the anode in order to enable a fuel cell reaction.

The anode may be disposed with a surface facing away from the anode surface on or in a substrate. In preferred fashion, the anode is made from a material that is permeable for the second substance and/or protons and/or preferably hydrogen or that is capable of storing the second substance and/or protons and/or preferably hydrogen in at least its surface.

The anode may be fashioned from palladium or may exhibit palladium. In this way, hydrogen can penetrate the anode and through it reach the membrane, through which the protons then pass to the cathode if an external circuit is closed.

Higher concentrations can be detected through a suitable choice of material for the reservoir or the hydrogen-sensitive film.

The substrate may be made from silicon. This enables simple fabrication as a semiconductor component, in particular as a fuel cell on a semiconductor substrate manufacturable in CMOS-compatible fashion.

The anode in the as-furnished condition and/or in a standard operational condition is free of the second substance. A current flow is thus prevented from arising as soon as the sensor fuel cell is installed; a voltage arises, and thus a current flow through a connected circuit or other components is enabled, only upon later detection of the medium corresponding to the second substance, in particular hydrogen. The system advantageously delivers a sensor signal only when the gas to be detected is ambient. It is thus self-activating or a passive sensor system that generates energy upon detecting hydrogen.

In preferred fashion, the sensor fuel cell is configured and arranged for a reaction of oxygen as the first substance and a hydrocarbon-containing substance, such as hydrogen, as the second substance.

Independently advantageous, moreover, is a sensor system having a sensor fuel cell so fashioned and having at least one component processing a sensor signal, the sensor fuel cell being connected to furnish the sensor signal as a voltage and/or current flow from the sensor fuel cell when both the substances are present in the environment of the sensor fuel cell. An "unlimited running time" can thus be guaranteed because the sensor system supplies itself with the reactants from the environment. In the measuring process, the sensor system delivers energy that can be used to supply the sensor system with energy or to process acquired measurements and/or the sensor signal.

A variety of exemplary applications may be implemented, such as a hydrogen sensor for detecting high hydrogen concentrations, in particular detonating gas mixtures. A CMOS hydrogen sensor system having SG FET and Lundström and a sensor fuel cell may also be implemented for determining the hydrogen concentration from the ppm range up to the high percent range. A self-activating threshold sensor having long service life for detecting explosive detonating gas mixtures can also be implemented in this way.

It is even possible to construct an autonomous hydrogen sensor system including a radio device. Upon detecting hydrogen, the sensor system generates the power necessary to activate the sensor system so that the measurement signal, for example a threshold value of a detonating gas, can subsequently be transmitted to a central station.

These and other objects, features and advantages of the present invention will become more apparent in light of the following detailed description of preferred embodiments thereof, as illustrated in the accompanying drawings.

DETAILED DESCRIPTION OF THE INVENTION

Figure 1:
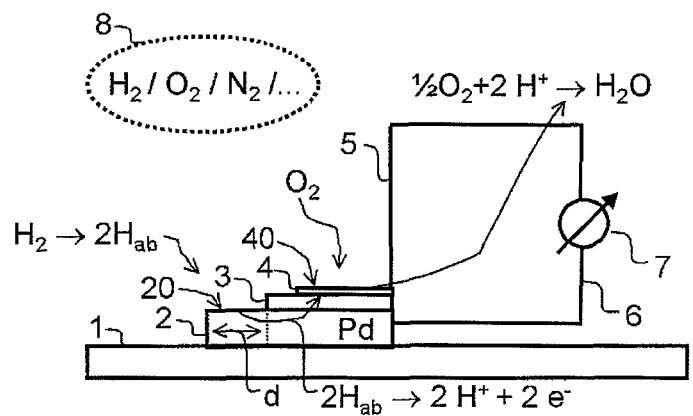
FIG. 1 depicts in side view of a sensor fuel cell.
Figure 2:
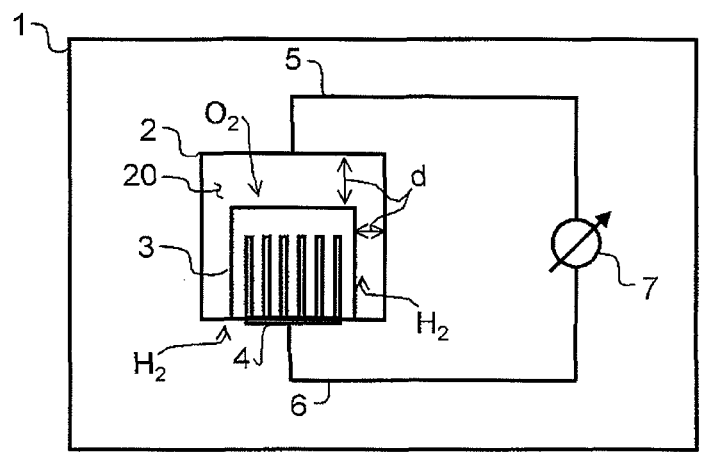
FIG. 2 depicts this sensor fuel cell of FIG. 1 in top view.

FIGS. 1 and 2 illustrate a hydrogen-sensor fuel cell (e.g., CMOS) on a semiconductor substrate 1. The substrate 1 is preferably silicon.

A catalytically active anode 2 is located on the substrate 1, and is preferably made from palladium deposited on the substrate as a palladium film. On a surface opposite the substrate 1, the catalytically active anode 2 provides an anode surface 20 that is partially covered by further fuel cell components and remains partially accessible an environment 8. An ambient second substance $H_2$, in particular a reactant in the form for example of hydrogen, can reach the anode surface 20 via the environment 8.

Here the term environment denotes a space that is not corporeally connected to the sensor fuel cell, such as in particular the region of air surrounding the sensor fuel cell and its support. Employment is also possible, however, in a fluid or a liquid, which then fill up the environment space.

Disposed on the remaining part of the anode surfaces 20 is a proton-conductive membrane 3. A cathode 4 partially or completely covers the membrane 3, and is located on a surface of the membrane 3 opposite the anode surface 20. A cathode surface 40 is also free to the environment 8, so that from the environment 8 a first substance, for example oxygen $O_2$, can pass to the cathode surface 40.

It is thus essential that the cathode surface 40 is at least partially exposed to the free environment 8, and also that at least a part of the anode surface 20 of the catalytically active anode 2 is freely accessibly exposed to the environment 8.

It is not mandatory that the same environment 8 have access to the cathode surface 40 and the anode surface 20. In principle a separation is also possible, so that the anode surface 20 is accessible to a different spatial environment region than the cathode surface 40. In this case, it would be necessary that at least the first substance be supplied to the environment of the cathode surface 40 and at least the second substance $H_2$ to the anode surface 20 via the distinct environment regions.

One or a plurality of components 7 processing a sensor signal can be connected to the two electrodes, that is, to the anode 2 or to the cathode 4, via contacts or conductors 5, 6. Upon the occurrence of for example oxygen as first substance and hydrogen as second substance in environment 8 and also further substances, if any, in the environment, the hydrogen passes into the anode 2 via the uncovered surface thereof and a fuel cell reaction of hydrogen and oxygen to water takes place with the liberation of electric power. Such a sensor fuel cell disposition is consequently passive if one of the two substances $O_2$, $H_2$ is absent, while this disposition becomes active if the other of the two substances $H_2$, $O_2$ additionally occurs in the environment 8 and reaches the corresponding one of the two electrodes.

Thus there is a self-activating sensor fuel cell. The current to be measured and the cell voltage, thus the cell power, are directly related to the concentration of hydrogen in the anode and thus to hydrogen in the environment 8, on the assumption of ordinary environments having a sufficient oxygen content.

It is thus preferably also possible to furnish a sensor system having such a component processing the sensor signal and having such a sensor fuel cell, the sensor signal being furnished as the voltage and/or the current flow of the sensor fuel cell if both the substances $O_2$, $H_2$ are present in the environment 8 of the sensor fuel cell. The electric power arising in the sensor fuel cell when both substances $O_2$, $H_2$ are present can thus be utilized for the purpose of treating the sensor signal as a measurement signal and further processing it in appropriate fashion. Advantageous in particular is that such a sensor system places itself in the active condition as a measurement system when both substances $O_2$, $H_2$ are present and at the same time is supplied with sufficient electric energy to operate the sensor system, provided certain threshold values of the quantities of the two substances $O_2$, $H_2$ for generating sufficient electric power are exceeded in the environment 8.

Particularly preferred is a sensor fuel cell in the form of an integrated circuit fuel cell, anode 2, preferably of palladium Pd, the proton-conductive membrane, preferably of tantalum pentoxide $Ta_2O_5$, and the catalytically active cathode, preferably of platinum Pt, being deposited as thin films on a substrate, preferably of silicon Si. However, one of ordinary skill in the art will recognize that other embodiments may be provided that use the inventive aspects of the present invention.

As an alternative instead of a film to store and/or convey hydrogen, there can be a catalytically active anode 2 that oxidizes hydrocarbons, for example methanol, ethanol or sugar, and liberates the resulting energy upon detection. In this way other second substances, in particular oxidizable gases, fluids or liquids, can also be detected with such a sensor fuel cell.

There may also be further components, such as a wireless interface and components that generate a radio signal upon detection of both substances and thus activation of the sensor system and transmit the radio signal via such the wireless interface to a remote central station. Naturally, other interfaces are also possible, such as for example hard-wired interfaces, in order to detect an activation of such a sensor system and, as appropriate, to transmit an intensity of the quantities of the substances acquired.

Although the present invention has been illustrated and described with respect to several preferred embodiments thereof, various changes, omissions and additions to the form and detail thereof, may be made therein, without departing from the spirit and scope of the invention.

What is claimed is:

1. An integrated circuit sensor fuel cell that can be activated by a first substance in its environment, comprising:
   a semiconductor substrate;
   a first catalytically active electrode deposited onto the semiconductor substrate;
   a second electrode reacting with said first substance of a first environment, said second electrode including a second electrode surface at least partially exposed to the first environment; and
   a proton-conductive membrane that is disposed between the first electrode and the second electrode to convey protons through from the first electrode to the second electrode,
   wherein a first electrode surface of first electrode is partly freely exposed to one of said first environment or a second environment for access of and reacting with at least a second substance,
   wherein, when said first electrode reacts with said second substance and said second electrodes reacts with said first substance, said sensor fuel cell generates a signal which is directly related to the concentration of said second substance in said one of said first environment or said second environment, and
   wherein the membrane and the second electrode are so sized and disposed on the first electrode surface that the first electrode surface is at least partially not covered by the membrane and the second electrode.

2. The sensor fuel cell of claim 1, wherein, between an outer circumference of the membrane and an outer circumference of the second electrode, in an extent in a plane of the first electrode surface, there remains a free clearance (d) to an outer circumference of the first electrode surface, via which the first electrode surface is freely accessible to the one of said first environment or said second environment for access of at least one second substance from the environment.

3. The sensor fuel cell of claim 1, wherein the first electrode is an anode.

4. The sensor fuel cell of claim 3, wherein the anode is fashioned from a material that is permeable for the second substance and/or protons and/or hydrogen or capable of storing the second substance and/or protons and/or hydrogen in at least its surface.

5. The sensor fuel cell of claim 3, wherein the anode comprises palladium.

6. The sensor fuel cell of claim 5, wherein the substrate comprises silicon.

7. The sensor fuel cell of claim 5, wherein the anode in the as furnished condition and/or in a standard operational condition is free of the second substance.

8. The sensor fuel cell of claim 5, fashioned for a reaction of oxygen as first substance and a hydrocarbon-containing substance as second substance.

9. A sensor fuel cell that is activated by a first substance in its environment, the fuel cell comprising:
   a catalytically active anode having an anode surface that is partially exposed to the environment to facilitate that a second substance is transferred from the environment to the anode;
   a cathode having a cathode surface that is partially exposed to the environment;
   a proton-conductive membrane arranged between the anode and the cathode, the membrane being configured such that protons are conducted from the anode to the cathode; and
   wherein the second substance is transferred to the anode via the exposed anode surface, and
   wherein the anode is arranged on a substrate such that a lower surface of the anode is arranged completely on or in the substrate.

10. The sensor fuel cell according to claim 9, wherein a component that is configured to process a sensor signal is connectable to the anode and the cathode.

11. The sensor fuel cell according to claim 9, wherein a component processes a sensor signal if both oxygen and hydrogen are present in the environment.

12. The sensor fuel cell according to claim 11, wherein the sensor signal is a voltage and/or a current flow of the sensor fuel cell.

* * * * *